(12) United States Patent
Sack et al.

(10) Patent No.: US 11,642,227 B2
(45) Date of Patent: May 9, 2023

(54) DYNAMIC DISC ASSEMBLY

(71) Applicant: Institute for Musculoskeletal Science and Education, Ltd., King of Prussia, PA (US)

(72) Inventors: James A. Sack, Elverson, PA (US); Seth Anderson, Mount Gretna, PA (US); John Peloza, King of Prussia, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 14 days.

(21) Appl. No.: 17/180,099

(22) Filed: Feb. 19, 2021

(65) Prior Publication Data
US 2022/0008214 A1    Jan. 13, 2022

Related U.S. Application Data

(60) Provisional application No. 62/951,168, filed on Dec. 20, 2019.

(51) Int. Cl.
*A61F 2/44*    (2006.01)
*A61F 2/30*    (2006.01)

(52) U.S. Cl.
CPC .. *A61F 2/4425* (2013.01); *A61F 2002/30136* (2013.01); *A61F 2002/30192* (2013.01); *A61F 2002/30224* (2013.01); *A61F 2002/30462* (2013.01); *A61F 2002/30528* (2013.01); *A61F 2002/30632* (2013.01); *A61F 2002/443* (2013.01)

(58) Field of Classification Search
CPC ............ A61F 2/4425; A61F 2002/4433; A61F 2/4465; A61F 2002/30136; A61F 2002/30192
See application file for complete search history.

(56) References Cited

U.S. PATENT DOCUMENTS

| 4,759,766 A | 7/1988 | Buettner-Janz et al. |
| 5,401,269 A | 3/1995 | Büttner-Janz et al. |
| 2002/0111685 A1 | 8/2002 | Ralph et al. |
| 2003/0220691 A1 | 11/2003 | Songer et al. |

(Continued)

OTHER PUBLICATIONS

International Search Report and Written Opinion dated Jul. 26, 2021 in PCT Application No. PCT/US2021/018784.

(Continued)

*Primary Examiner* — Matthew J Lawson
(74) *Attorney, Agent, or Firm* — Plumsea Law Group, LLC

(57) ABSTRACT

A dynamic disc assembly has a superior end plate, an inferior end plate, and a core. The core has surfaces of an annular Fresnel shape and a linear Fresnel-like shape combined to control the dynamic range of motion (ROM) movement arranged to match anatomical ROM. The core is interposed between and held against interior surfaces of the superior end plate and the inferior end plate. The assembly further has a pair of coupling cords, one coupling cord at each lateral end of the superior and inferior end plates wherein each lateral end of each end plate has one or more cord connections attached and affixed to the coupling cord to form and retain the dynamic disc assembly.

23 Claims, 7 Drawing Sheets

(56) References Cited

U.S. PATENT DOCUMENTS

| | | | |
|---|---|---|---|
| 2005/0203626 A1* | 9/2005 | Sears | A61F 2/4425 623/17.11 |
| 2006/0015183 A1* | 1/2006 | Gilbert | A61F 2/4425 623/17.11 |
| 2006/0025777 A1* | 2/2006 | Weber | A61F 2/4611 606/99 |
| 2006/0293752 A1* | 12/2006 | Moumene | A61F 2/4425 623/17.13 |
| 2007/0100454 A1* | 5/2007 | Burgess | A61B 17/025 623/17.14 |
| 2007/0185578 A1 | 8/2007 | O'Neil et al. | |
| 2010/0100185 A1* | 4/2010 | Trieu | A61F 2/4425 623/17.11 |
| 2010/0137992 A1 | 6/2010 | Büttner-Janz et al. | |
| 2010/0234954 A1* | 9/2010 | Justis | A61F 2/4425 623/17.12 |
| 2011/0196498 A1 | 8/2011 | Biedermann et al. | |
| 2016/0030193 A1 | 2/2016 | Ferree et al. | |

OTHER PUBLICATIONS

International Preliminary Report on Patentability dated Jun. 30, 2022 in PCT Application No. PCT/US2021/018784.

* cited by examiner

RANGE OF MOTION FOR EACH LUMBAR DISC
AS AN AVERAGE DESIGN TARGET

|  | L1-L2 | L2-L3 | L3-L4 | L4-L5 | L5-S1 |
|---|---|---|---|---|---|
| FLEXION/EXTENSION | 12° | 14° | 15° | 16° | 17° |
| LATERAL FLEXION | 6° | 6° | 8° | 6° | 3° |
| AXIAL ROTATION | 2° | 2° | 2° | 2° | 1° |

FIG. 7

DYNAMIC DISC ASSEMBLY

CROSS-REFERENCE TO RELATED APPLICATIONS

This application claims the benefit of U.S. Provisional Patent Application No. 62/951,168, filed on Dec. 20, 2019, and titled "Dynamic Disc Assembly," the entire disclosure of which is hereby incorporated by reference.

BACKGROUND

The present disclosure relates to an artificial dynamic disc assembly. Artificial intervertebral discs are an alternative to spinal fusion. These spinal implants are designed to restore or maintain the appropriate alignment and spacing of adjacent vertebral bodies. In addition, an artificial disc is also designed for kinematic behavior similar to a healthy natural disc. Known artificial disc concepts use numerous means for providing motion and stiffness similar to a natural healthy disc, to include the adaptation of elastomers, mechanical springs, and articulating surfaces.

An alternative to spinal fusion is replacement of the damaged disc with a motion preservation device, which includes either a nucleus or total disc replacement (TDR). The rationale for the development of the artificial disc is to prevent adjacent segment disease. Artificial disc devices can be broadly divided into two categories, those that replace the nucleus only, leaving the annulus and vertebral body end plates intact and those that involve replacement of the disc and addition of prosthetic end plates. Both strategies are directed at restoration of intervertebral disc function.

Prior art artificial discs have a larger height due to the need to contour the lens shaped disc, and the range of motion is generally equal in all directions, with needed curvature to compliment the adjacent vertebrae. Also range of motion (ROM) is not ideal for any given direction and typically quite limited. Noticeably, the hard ROM stops that exist have been the source of an audible clunking sound after being implanted. The surface area being a small area not matching the articulating contour results in high wear rates. The small load bearing area results in high wear rates and lack of resistance to shear loads such as would be found at L5-S1 at approximately 45 degrees. The elastomer load bearing existing designs tend to overload and destroy the facet joints due to excessive non-anatomical ROM. Elastomer degradation due to high sustained loads is a problem for implant longevity in almost all prior art discs using an elastomeric nucleus.

The present invention as disclosed herein solves these limitations by providing a structural advantage not found in existing artificial disc designs.

SUMMARY

A dynamic disc assembly has a superior end plate, an inferior end plate, and a core. The core has surfaces of an annular Fresnel shape and a linear Fresnel-like shape combined to control the dynamic range of motion movement arranged to match anatomical ROM. The core is interposed between and held against interior surfaces of the superior end plate and the inferior end plate. The assembly further has a pair of coupling cords, one coupling cord at each lateral end of the superior and inferior end plates wherein each lateral end of each end plate has one or more cord connections attached and affixed to the coupling cord to form and retain the dynamic disc assembly.

The core has a first inferior surface being an annular Fresnel lens shaped surface configured to articulate about a complimentary Fresnel lens shaped surface of the interior surface of the inferior end plate, wherein a clearance between the first inferior surface of the core relative to the interior surface of the inferior end plate allows for articulating range of motion (ROM) movements in any direction of rotation, wherein the annular Fresnel lens shaped surface forms ROM stops limiting angular movement. The core has a second superior surface having a linear Fresnel like shape configured to articulate in an anterior and posterior position, but not a lateral position (flexion and distraction); a complimentary linear Fresnel like shaped surface of the interior surface of the superior end plate wherein a clearance between the second superior surface of the core relative to the interior surface of the superior end plate allows for the articulating range of motion anteriorly and posteriorly wherein the linear Fresnel like shaped surface form ROM stop limiting the posterior and anterior movement of the superior end plate relative to the core and prevents lateral movement. The annular Fresnel shaped surfaces permit rotation and 3 to 8 degrees of bending in flexion distraction and lateral distraction. The linear Fresnel shaped surfaces permit 7 to 12 degrees of bending in flexion and distraction with no lateral bending or rotation. The annular and linear shaped mating surfaces may be reversed if needed.

Each of the coupling cords includes a plurality of elastomeric ROM control dampers. Each of the one or more cord connections is configured as a "J" shaped hook configured to connect directly to the coupling cord. In the preferred embodiment, the superior end plate has one connection on one lateral end and two connections on an opposing lateral end and the inferior end plate has one connector on the lateral end connected to the coupling cord on the same lateral end of the superior end plate having two connectors and has two connectors connected to the coupling cord on the same lateral end of the superior end plate having one connection. This results in an alternating inner locking mechanism with gaps to contain the dampers. The coupling cord is made of high strength non-absorbable suture material and forms a high strength tensile member keeping the assembly of end plates securely attached as they hold the core in place therebetween. The high strength suture material is HMW PE Nylon, Prolene, Silk, or other biocompatible fiber in a monofilament structure or a multifilament.

The ROM control dampers are preferably silicone or a PU-PC blend. The ROM control dampers are over-molded onto the coupling cord, or alternatively the ROM control dampers are a cylinder shape bonded or otherwise adhesively fixed to the coupling cord.

The superior and inferior end plates each have an exterior surface complimentarily contoured and configured to support an end plate of an adjacent vertebral body when implanted. Each exterior surface preferably has a bone growth promoting texture.

In one embodiment, the superior and inferior end plate each have an integral steerable keel extending between lateral ends and curved to directionally turn the disc on implantation when implanted along an oblique or OLIF approach.

The disc has a low profile height configured and sized to fit a 9 mm to 16 mm high disc space. The elastomeric ROM control dampers and the cord connections limit rotation to an anatomical 2 degrees or less. Preferably, the interior surfaces of the superior and inferior end plates are coated to decrease wear. The coated interior surfaces have a coating of one of TIN or B-Ti3-Au.

The disc assembly of the present invention can pivot in extension in the range of 10 to 20 degrees; in lateral flexion in the range of 2 to 10 degrees, and to rotate in the range of 1 to 5 degrees. More preferably, the disc assembly of the present invention can pivot in extension in the range of 12 to 17 degrees; in lateral flexion in the range of 3 to 8 degrees, and to rotate in the range of 1 to 2 degrees. All of these range of motion features can be tuned to the specific vertebral disc location and sized to fit the anatomy of the patient.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 7 is a chart showing Range Of Motion for each Lumbar Disc as an average design target of the dynamic disc of the present invention.

DETAILED DESCRIPTION

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs. It is to be understood that this invention is not limited to the particular methodology, protocols, and constructs described herein. It is also to be understood that the terminology used herein is for the purpose of describing particular embodiments only, and is not intended to limit the scope of the present invention which will be limited only by the appended claims.

OLIF—or oblique lateral interbody fusion, is a less invasive approach to spinal fusion surgery in which the neurosurgeon accesses and repairs the lower (lumbar) spine from the front and side of the body (passing in a trajectory about halfway between the middle of the stomach and the side of the body). During an OLIF procedure, the surgeon uses a corridor between the psoas muscle and the peritoneum to access the spine. The psoas muscles connect the lower back to the thighs and enable movement and flexibility of the back, pelvis, legs, and hips. The peritoneum is the membrane that lines the abdominal cavity.

Psoas—The psoas is a deep-seated core muscle connecting the lumbar vertebrae to the femur. The psoas major is the biggest and strongest player in a group of muscles called the hip flexors: together they contract to pull the thigh and the torso toward each other.

Fixedly attached—shall refer to two components joined in a manner such that the components may not be readily separated (for example, without destroying one or both components). In contrast, the term "removably attached" shall refer to components that are attached to one another in a readily separable manner (for example, with fasteners, such as bolts, screws, etc.).

Figure 1:
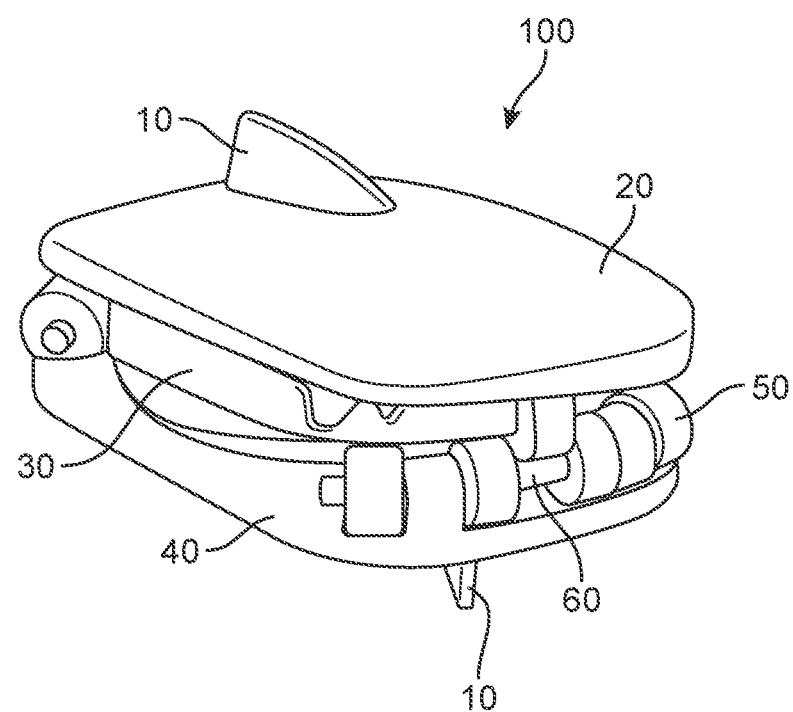
FIG. 1 is a perspective view of a first embodiment of the dynamic disc assembly of the present invention showing a curved keel on superior and inferior end plates.

With reference to FIGS. 1-6, embodiments of a dynamic disc assembly 100 are illustrated. As shown in FIG. 1, in some embodiments, the dynamic disc assembly 100 has a steerable keel 10 extending from an exterior surface of the superior end plate 20 and the inferior end plate 40. As shown, the steerable keel 10 is uniquely configured to be curved so that when the dynamic disc assembly 100 is inserted between vertebral bodies using an oblique approach such as an OLIF approach the dynamic disc assembly 100 can be fed into the approach, and as entering between the vertebral bodies, the steerable keel 10 will turn the dynamic disc assembly 100 in such a fashion that it is in proper alignment and position with the vertebral bodies. In a first embodiment using the OLIF approach for implantation, the steerable keel 10 is an optional feature that can be used or not used depending on the approach the surgeon is attempting to make during the implantation. The remaining embodiments FIGS. 2-6 show the same dynamic disc assembly 100 but with the optional keel 10 not shown. It is understood that both with the keel 10 or without the keel 10, all other components are identical throughout this written description.

Figure 2:
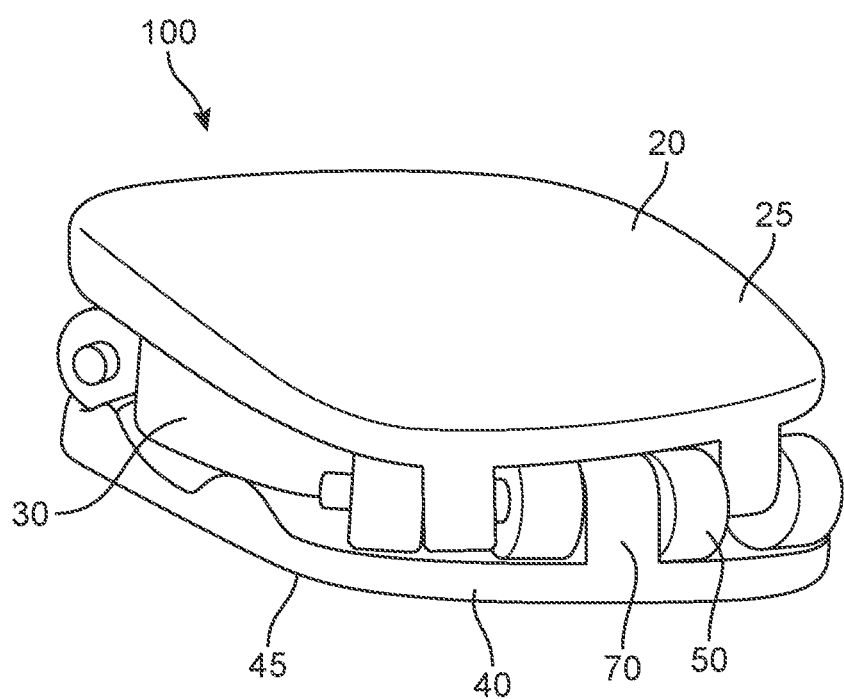
FIG. 2 is a perspective view of a second embodiment of the dynamic disc assembly.
Figure 3:
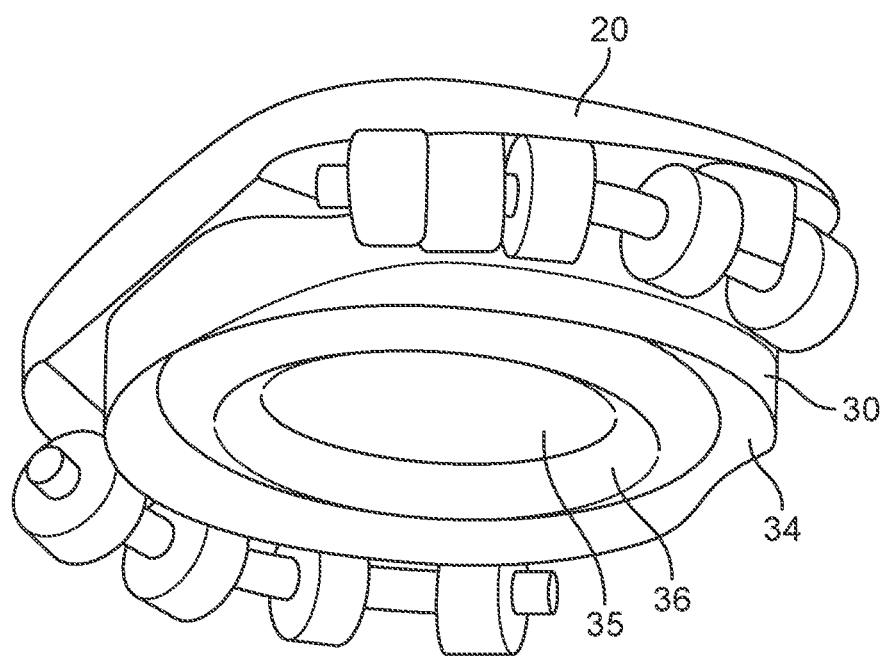
FIG. 3 is a bottom perspective view of the dynamic disc assembly of FIG. 2.
Figure 10:
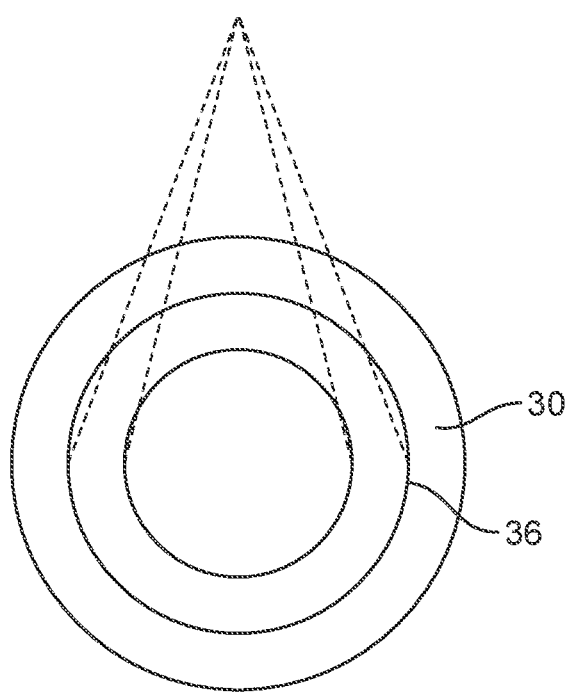
FIG. 10 shows the annular Fresnel lens shape surface when extended converges to a point.

With reference to FIG. 2, the dynamic disc assembly 100 is illustrated having a superior end plate 20 and an inferior end plate 40 and, sandwiched therebetween, a core 30. The core 30 is surrounded on lateral ends by coupling cords 60 with elastomeric range of motion dampers 50. As illustrated in FIG. 2, four dampers 50 are employed on each lateral end. Further illustrated with reference to FIG. 3, the superior end plate 20 is shown having the central core 30 with an inferior surface 34 shown, this inferior surface 34 of the central core 30 forms an annular Fresnel lens shaped configuration having a slightly hemispherical center 35 with a ring of annular ridges 36. With reference to FIG. 10, it is important to note this particular shape is designed such that when one projects center lines from the curved ridges 36, the lines will project to a point. This is a particularly useful feature in that as the core 30 is sandwiched between the superior and inferior end plates 20, 40, complimentary shaped features grooves 46 are on the interior of the adjacent plate 40 to which the core 30 is resting and complimentary grooves 26 of plate 20.

Figure 5:
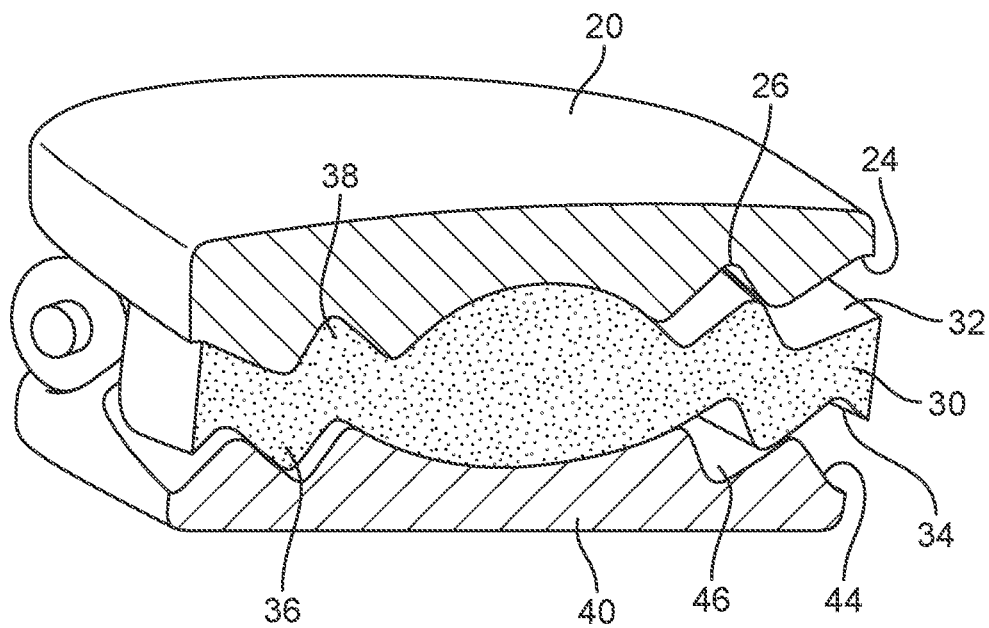
FIG. 5 is a cross sectional perspective view of the dynamic disc assembly cut from a posterior to anterior section.
Figure 6:
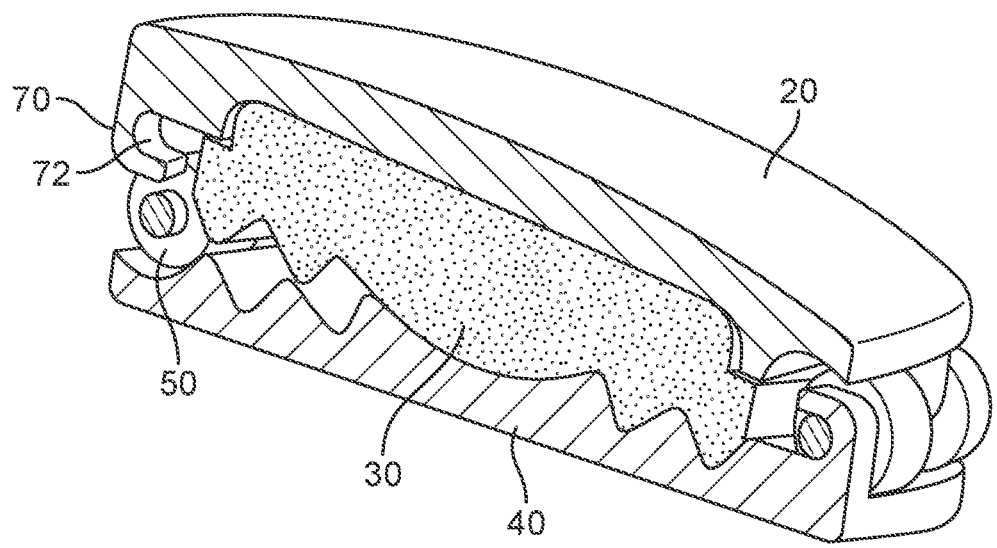
FIG. 6 is a cross sectional perspective view of the dynamic disc assembly cut across the lateral ends.

For example, as shown in FIGS. 5 and 6, cross sectional views of the dynamic disc assembly 100 are shown. The annular Fresnel lens shaped inferior surface 34 of the core 30 is shown resting on the inferior plate 40 interior surface 44 and there is provided clearances such that the core 30 can move relative to the inferior plate 40 as illustrated. The limits of the movement are constrained by the annular ridges 36 surrounding the hemispherical center of the core 30 relative to the inferior plate 40. The inferior plate 40 and central core 30 are capable of moving rotationally in any direction. This is limited by the coupling cords 60 and the elastomeric dampers 50 that assist in preventing complete rotation of the inferior plate 40 relative to the core 30.

Figure 4:
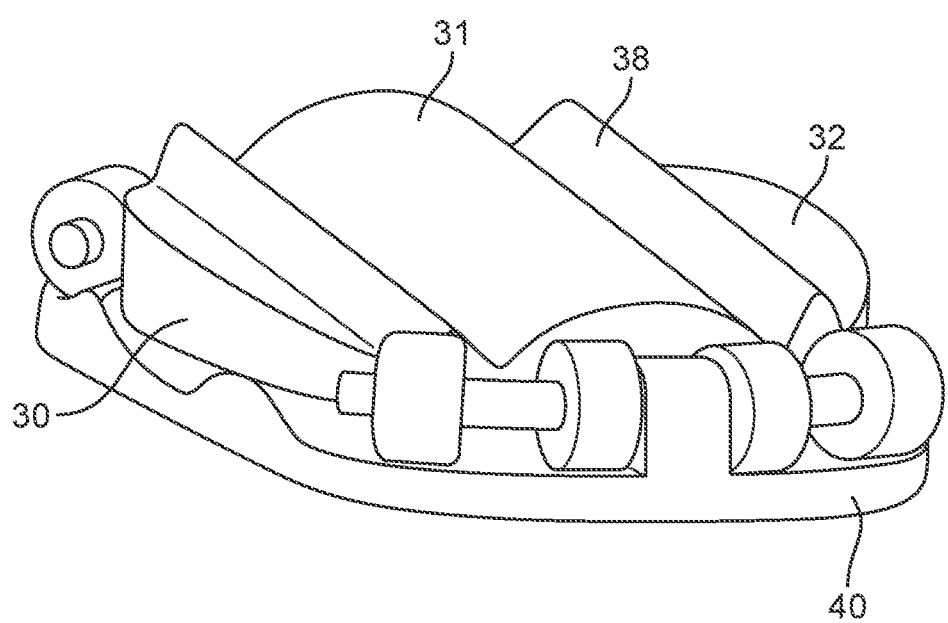
FIG. 4 is a top perspective view of the dynamic disc assembly of FIG. 2.
Figure 11:
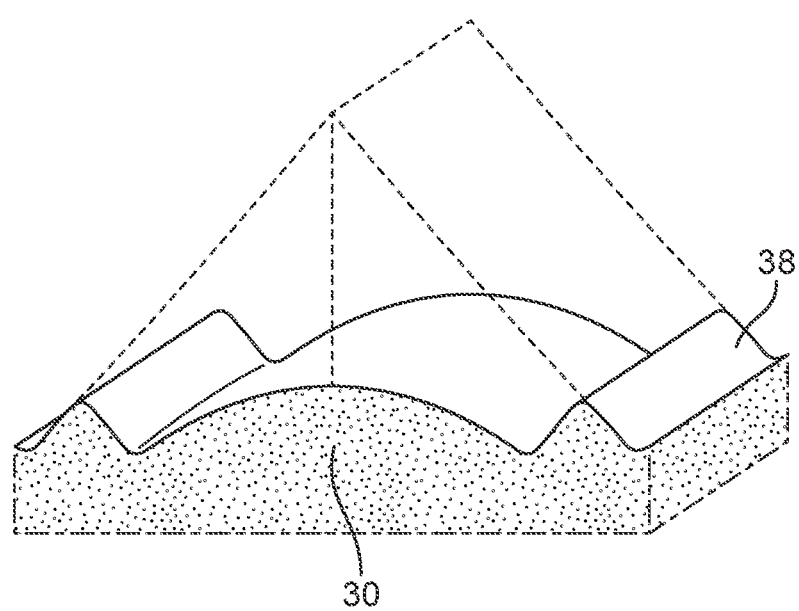
FIG. 11 shows the linear Fresnel like shape surface when extended projects to a line.

With reference to FIG. 4, the opposite surface of the core 30 is shown, this is the superior surface 32 of the core 30 and it fits a complimentary interior surface 24 of the superior end plate 20. As shown, the core superior surface 32 is cylindrical in shape at the center 31 bounded on each side by a linear ridge 38, these linear ridges 38 and the cylindrical center 31 contour of the superior surface 32 of the core 30 is such that when center lines are projected from the curved surfaces of the central core 30 adjacent to the ridges 38 instead of coming to a central point, as shown in FIG. 10, as was done in the core's 30 annular Fresnel shaped ring on the inferior surface 34, the core's 30 Fresnel-like shaped linear lens superior surface 32 has the ridges 38 extend to a projected line, as shown in FIG. 11, where they converge along the path of the ridges 38. Due to this feature, the superior plate 20 when positioned complimentary as shown in FIGS. 5 and 6 has the interior surface 24 conveniently fitting with a sufficient amount of clearance with the core 30 that they can provide certain relative movement in the posterior and anterior direction. However as shown in FIG. 5 in particular, this movement is limited such that the surfaces 32, 24 cannot move in a lateral direction. The limitation is such that the movement allows for certain flexion extension to occur when the assembly is put together but prevents the superior plate 20 from significant lateral movement.

The articulating superior and inferior surfaces 32, 34 of the core 30 and the interior surfaces 24, 44 of the end plates 20, 40 create articulating surfaces that are shaped like Fresnel lenses, allow for a minimization of the overall height of the disc assembly 100 and also maximize the surface area to support the loads when the disc 100 is implanted. Preferably, the exterior surfaces 25, 45 of the superior and inferior end plates 20, 40 have bone growth promoting texture, these bone growth promoting textures enable the surface to compatibly fit between the vertebral bodies and engage the vertebra in such a way that over time they exhibit a certain amount of new bone ingrowth. The rings of motion stops are produced by the Fresnel lens shapes in both superior and inferior 20, 40 mating complimentary surfaces 32, 34 coupled to the core 30, this assists by acting as shear load stops that allows the use in L5-S1 load paths of 45 degrees off axis.

Large and dispersed support surface decrease pressure per a given area and permit much thinner superior and inferior end plates 20, 40 and core 30. This feature allows the production of the dynamic disc 100 of the present invention to be able to fit into a 9 mm high disc space if desired, preferably the disc height is between 9 mm and 16 mm, but as low as 9 mm can be achieved.

It must be recognized that the prior art disc implants do not provide a disc height of compact construction and assembly due to the limitations on the surface area and the numerous mechanical parts that are used to create an artificial disc. As is commonly found in the prior art, the smaller load bearing load areas result in high wear rates and lack of resistance to shear loads, such as in the L5-S1 area at approximately 45 degrees. Also, prior art artificial discs produced a loud clunking sound when they achieved stops are abruptly contacted, the audible sound is a problem for implant longevity as it results from an impact occurring every time the disc approaches an end of range of motion.

The present invention's use of end of range of motion dampers 50 at lateral ends to limit the amount of impact that can occur primarily due to the fact that as the superior and inferior end plates 20, 40 come to an end of range of motion, the core 30 which is going to create an abrupt stop is assisted by the elastomeric dampers 50 such that there is a cushioning effect that occurs as the disc assembly 100 reaches the limit of its range of motion.

Figure 8:
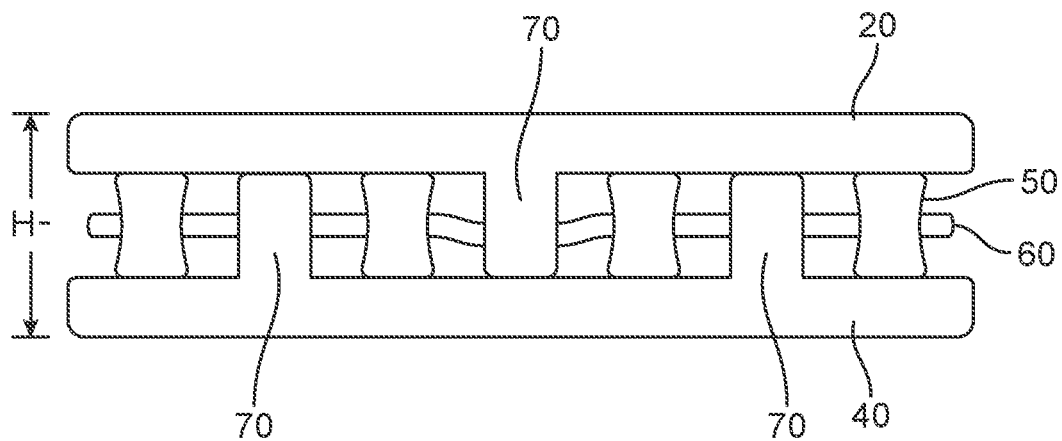
FIG. 8 is a view of the dynamic disc in a compressed position showing the ROM dampers compressed against interior surface of the superior and inferior end plates.
Figure 9:
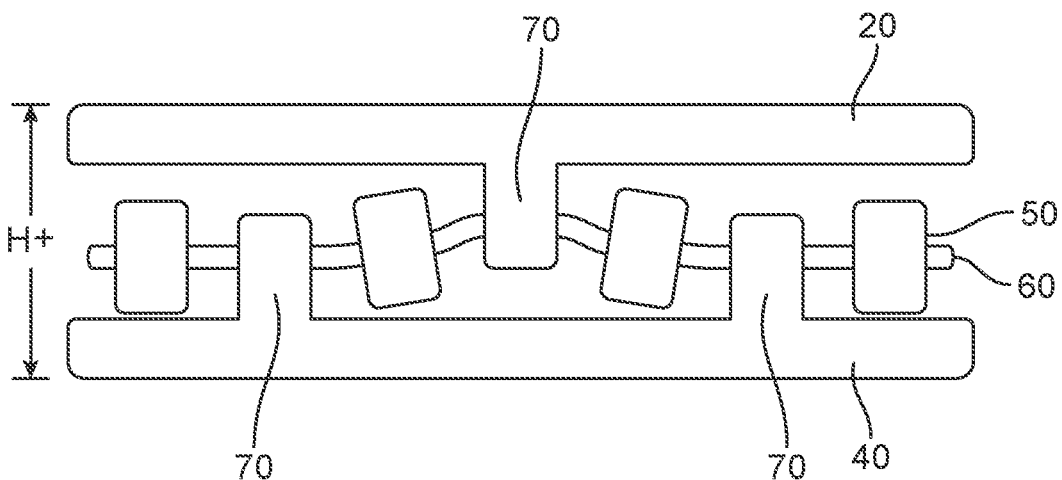
FIG. 9 is the opposite side of the dynamic disc showing the superior and inferior end plates moved apart with the coupling cord and cord connection pulled in tension.

With reference to FIGS. 8 and 9, it is important to note that the coupling cords 60 are connected to the end plates 20, 40 by connections 70, the connections 70 are in the shape of a "J" hook having an opening 72 that allows the connection 70 to snap over the cord 60 between the elastomeric control dampers 50. As shown in the embodiments, one lateral end of the superior end plate 20 has a pair of connections 70 while the opposite end has a single connection 70. The inferior plate 40 has a single connection 70 that when coupled to the cords 60 connects on the side where the superior plate 20 has two connections 70, accordingly these connections are between adjacent control dampers 50 as shown. As the implant increases in footprint size the number of connections 70 may also increase to bear the added load. When the disc assembly 100 deflects to a maximum deflection, control dampers 50 are somewhat compressed between the endplates 20, 40 as they reach a stop creating a relatively low height on that side of the disc assembly 100. On the opposite side where the angulation is pulling the end plates 20, 40 apart, the coupling cord 60 achieves a somewhat sinusoidal shape as it is being pulled in one direction by the central connection 70 of one end plate and the opposite direction by the pair of connections 70 on the opposing end plate. This type of movement can occur back and forth. The coupling cords 60 provide a tensile member that keeps the assembly together and provides for smooth movement in any direction with limits on the lateral position.

With reference to the dynamic disc assembly 100 of the present invention, a chart is shown in FIG. 7 wherein specific vertebral bodies, L1-L2, L2-L3, L3-L4, L4-L5, L5-S1 are listed. Due to the construction as described herein, the movement and range of movement in the flexion extension can be tuned for each vertebral body, as shown a 12-17 degree range of motion is illustrated for the flexion/extension. The disc assembly 100 is able to pivot on a large surface area in lateral flexion 3 to 8 degrees. In axial rotation, uniformly a rotation of 2 degrees is permitted with the L5-S1 limited to 1 degree rotation. This is achieved by tuning the specific dynamic disc assembly 100 for the specific application.

To achieve this assembly, in some embodiments the coupling cord 60 may be over-molded or bonded such that the cord 60 retains the range of motion dampers 50 such that they are trapped into the connections 70 by impingement from disc assembly 100. Alternating hooks or connections 70 restrain tensile loads due to connection with the cord 60 embedded in the chain of dampers 50. Elastomeric dampers 50 or Bumpers permit soft stops for range of motion but are not normally sharing the load from body weight or lifting loads. This may increase the durability and life of the dynamic disc assembly 100.

Referring back to FIG. 3, it will be noted that the inferior surface 34 of the core 30 configured with the annular Fresnel shape permits rotation and 3 to 8 degrees of bending and flexion distraction and lateral distraction; whereas referring to FIG. 4, the superior surface 32 is configured to permit 7 to 12 degrees of flexion and distraction but not lateral bending or rotation. When the disc assembly 100 is put together the combination can be additive in flexion. As such, the table in FIG. 7 showing the desired angles of the dynamic disc assembly are easily achieved by these two unique surfaces.

It will be noted that the use of the Fresnel shaped annular lens with a complimentary linear Fresnel like shaped lens is a preferred embodiment, it is believe however that one could deviate slightly from annular shape such that the shape is created in more of an oval or non-Fresnel shape but achieves similar limitations with regard to the features. Accordingly, these and other variations can be made to the combination taught herein. For example, a disc assembly could be made with only annular inferior and superior core surfaces and limited in use as a disc with different characteristic features, however adopting the spirit and scope of the present invention. Alternatively, the linear Fresnel like configuration could be employed for both core surfaces as well, also limiting the features, any combination of the two is possible.

Additionally, as shown in FIG. 1, a curved steerable keel 10 is used. If a different approach is taken, it it will be appreciated that optional keels could be used that are less curved or even linear shaped depending on the approach of the implant chosen by the surgeon. Accordingly, these and other variations can be attempted when practicing the present invention.

Figure 12:
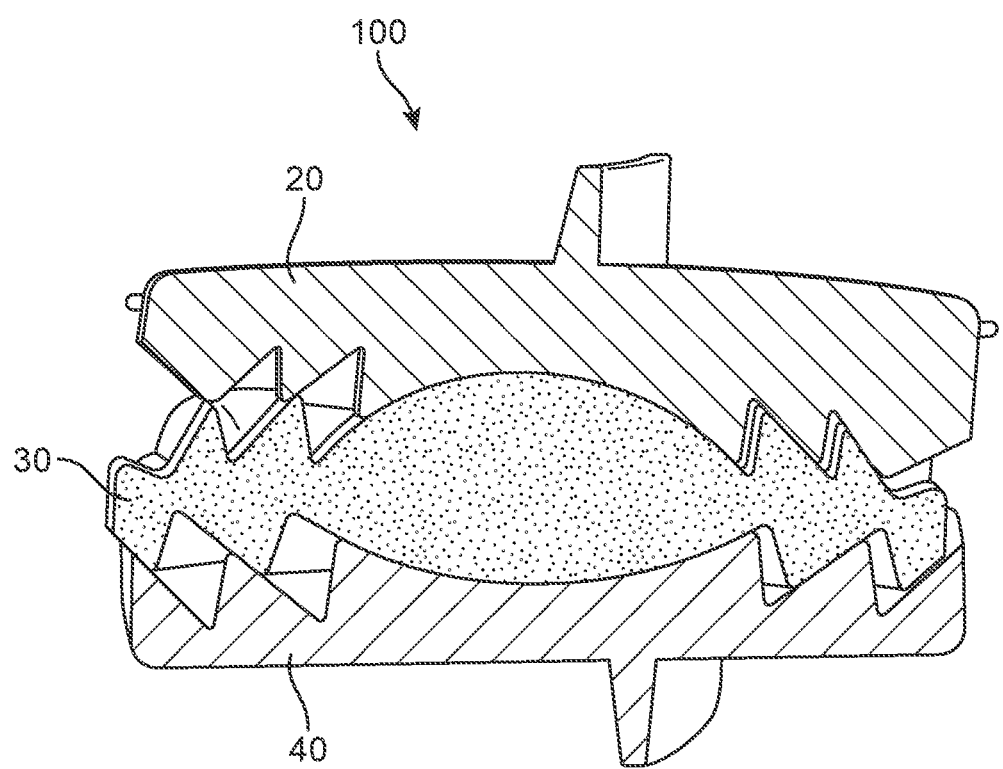
FIG. 12 is a cross sectional perspective view of the dynamic disc assembly.

With reference to FIG. 12, a picture of cross-section of the disc assembly is illustrated. Notice the angle of the stops and the radiused surfaces between them having a common center line or point. With the stops at this angle closer to vertical we gain surface area to support the weight and provide more positive shear resistance.

While various embodiments are described, the description is intended to be exemplary, rather than limiting and it will be apparent to those of ordinary skill in the art that many more embodiments and implementations are possible that are within the scope of the disclosed embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted. Further, unless otherwise specified, any step in a method or function of a system may take place in any relative order in relation to any other step described herein.

What is claimed is:

1. A dynamic disc assembly comprises;
   a superior end plate;
   an inferior end plate;
   a core interposed between and held against interior surfaces of the superior end plate and the inferior end plate; and
   wherein the core has an inferior surface being an annular Fresnel lens shaped surface configured to articulate about a complimentary Fresnel lens shaped surface of the interior surface of the inferior end plate, wherein a clearance between the inferior surface of the core relative to the interior surface of the inferior end plate allows for articulating range of motion (ROM) movements in any direction of rotation, wherein the annular Fresnel lens shaped surface of the core forms ROM stops limiting angular movement.

2. The dynamic disc assembly of claim 1 further comprises a pair of coupling cords, one coupling cord at each lateral end of the superior and inferior end plates, wherein each lateral end of each end plate has one or more cord connections attached and affixed to the coupling cord to form the dynamic disc assembly.

3. The dynamic disc assembly of claim 1 wherein the core has a superior, linear Fresnel like shaped surface configured to articulate in an anterior and posterior direction, but not a lateral direction;
   wherein the superior end plate includes a complimentary linear Fresnel like shaped surface of the interior surface of the superior end plate wherein a clearance between the second superior surface of the core relative to the interior surface of the superior end plate allows for the articulating range of motion anteriorly and posteriorly wherein the linear Fresnel like shaped surface of the core forms ROM stops limiting the posterior and anterior movement of the superior end plate relative to the core and prevents lateral movement.

4. The dynamic disc assembly of claim 2 wherein the annular Fresnel shaped surface permits rotation and 3 to 8 degrees of bending in flexion distraction and lateral distraction.

5. The dynamic disc assembly of claim 3 wherein the linear Fresnel shaped surface permits 7 to 12 degrees of bending inflexion and distraction with no lateral bending or rotation.

6. The dynamic disc assembly of claim 2 wherein each of the coupling cords includes a plurality of elastomeric ROM control dampers.

7. The dynamic disc assembly of claim 2 wherein each of the one or more cord connections is configured as a "J" shaped hook configured to connect directly to the coupling cord.

8. The dynamic disc assembly of claim 2 wherein the superior end plate has one connection on one lateral end and two connections on an opposing lateral end and the inferior end plate has one connector on the lateral end connected to the coupling cord on the same lateral end of the superior end plate having two connectors and has two connectors connected to the coupling cord on the same lateral end of the superior end plate having one connection.

9. The dynamic disc assembly of claim 2 wherein the coupling cord is made of high strength non-absorbable suture material.

10. The dynamic disc assembly of claim 9 wherein the high strength suture material is HMW PE Nylon, Prolene, Silk in a monofilament structure or a multifilament.

11. The dynamic disc assembly of claim 6 wherein the ROM control dampers are over-molded onto the coupling cord.

12. The dynamic disc assembly of claim 6 wherein the ROM control dampers are silicone or polyurethane polycarbonate blend.

13. The dynamic disc assembly of claim 6 wherein the ROM control dampers are a cylinder shape fixedly attached to the coupling cord.

14. The dynamic disc assembly of claim 1 wherein the superior and inferior end plates each have an exterior surface complimentarily contoured and configured to support an end plate of an adjacent vertebral body when implanted.

15. The dynamic disc assembly of claim 14 wherein each exterior surface has a bone growth promoting texture.

16. The dynamic disc assembly of claim 15 wherein at least one of the superior and inferior end plate has an integral steerable keel extending between lateral ends and curved to directionally turn the disc on implantation when implanted along an oblique or OLIF approach.

17. The dynamic disc assembly of claim 1 wherein the disc has a low profile height configured and sized to fit a 9 mm to 16 mm high disc space.

18. The dynamic disc assembly of claim 6 wherein the elastomeric ROM control dampers and the cord connections limit rotation to 2 degrees or less.

19. The dynamic disc assembly of claim 1 wherein the interior surfaces of the superior and inferior end plates are coated to decrease wear.

20. The dynamic disc assembly of claim 19 wherein the coated interior surfaces have a coating of one of TIN or B-Ti3-Au.

21. The dynamic disc assembly of claim 1 wherein the disc assembly can pivot in extension in the range of 10 to 20 degrees; in lateral flexion in the range of 2 to 10 degrees, and to rotate in the range of 1 to 5 degrees.

22. The dynamic disc assembly of claim 21 wherein the disc assembly can pivot in extension in the range of 12 to 17 degrees; in lateral flexion in the range of 3 to 8 degrees, and to rotate in the range of 1 to 2 degrees.

23. A dynamic disc assembly comprises;
   a superior end plate;
   an inferior end plate;
   a core interposed between and held against interior surfaces of the superior end plate and the inferior end plate; and
   wherein the core has a superior, linear Fresnel like shaped surface configured to articulate in an anterior and posterior direction, but not a lateral direction;
   wherein the superior end plate includes a complimentary linear Fresnel like shaped surface;
   wherein a clearance between the superior surface of the core relative to the interior surface of the superior end plate allows for an articulating range of motion (ROM) anteriorly and posteriorly wherein the linear Fresnel like shaped surface of the core forms ROM stops limiting the posterior and anterior articulation of the superior end plate relative to the core and prevents lateral articulation.

* * * * *